US012678149B2

(12) United States Patent
Eidenschink et al.

(10) Patent No.: US 12,678,149 B2
(45) Date of Patent: Jul. 14, 2026

(54) OCCLUDER MEDICAL DEVICE

(71) Applicant: St. Jude Medical, Cardiology Division, Inc., St. Paul, MN (US)

(72) Inventors: Tracee Eidenschink, Wayzata, MN (US); Andrea Stafford, New Brighton, MN (US); Erika Beek, Bloomington, MN (US); Michael P. Meyer, Minnestrista, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 223 days.

(21) Appl. No.: 17/669,685

(22) Filed: Feb. 11, 2022

(65) Prior Publication Data

US 2022/0257224 A1 Aug. 18, 2022

Related U.S. Application Data

(60) Provisional application No. 63/148,745, filed on Feb. 12, 2021.

(51) Int. Cl.
    *A61B 17/00* (2006.01)
(52) U.S. Cl.
    CPC ..................... *A61B 17/0057* (2013.01); *A61B 2017/00004* (2013.01); *A61B 2017/00597* (2013.01); *A61B 2017/00623* (2013.01); *A61B 2017/00628* (2013.01); *A61B 2017/00632* (2013.01); *A61B 2017/00867* (2013.01)

(58) Field of Classification Search
    CPC .. A61B 2017/0004; A61B 2017/00597; A61B 2017/00623; A61B 2017/00628; A61B 2017/00632; A61B 2017/00867
    See application file for complete search history.

(56) References Cited

U.S. PATENT DOCUMENTS

| | | | | |
|---|---|---|---|---|
| 6,652,555 B1* | 11/2003 | VanTassel | ........ | A61B 17/12022 606/151 |
| 6,726,704 B1* | 4/2004 | Loshakove | ........ | A61B 17/0057 606/213 |
| 7,033,393 B2* | 4/2006 | Gainor | .................. | A61F 2/4611 606/213 |
| 7,144,410 B2* | 12/2006 | Marino | .............. | A61B 17/0057 606/213 |
| 7,658,748 B2* | 2/2010 | Marino | .............. | A61B 17/0057 606/213 |
| 7,780,700 B2* | 8/2010 | Frazier | ............. | A61B 17/12122 606/151 |
| 7,930,016 B1* | 4/2011 | Saadat | ............... | A61B 1/00089 600/478 |
| 8,029,534 B2* | 10/2011 | Hruska | .............. | A61B 17/0057 606/213 |
| 8,974,488 B2 | 3/2015 | Tan et al. | | |
| 9,554,783 B2* | 1/2017 | Pavcnik | ............. | A61B 17/0057 |
| 9,788,840 B2 | 10/2017 | Marks et al. | | |
| 9,839,431 B2 | 12/2017 | Meyer et al. | | |

(Continued)

*Primary Examiner* — Alexander J Orkin

(74) *Attorney, Agent, or Firm* — SLEMAN & LUND LLP

(57) ABSTRACT

A medical device includes a device frame, including a proximal portion and a distal portion and configured to selectively transition between a collapsed configuration and an expanded configuration. The medical device also includes at least one cover, wherein at least one cover is coupled to at least one of the proximal and distal portions.

13 Claims, 9 Drawing Sheets

(56)         References Cited

U.S. PATENT DOCUMENTS

| | | | |
|---|---|---|---|
| 10,292,711 B2 | 5/2019 | Olson et al. | |
| 2003/0028213 A1* | 2/2003 | Thill | A61B 17/0057 |
| | | | 606/200 |
| 2003/0057156 A1* | 3/2003 | Peterson | A61B 17/12122 |
| | | | 210/645 |
| 2006/0276839 A1* | 12/2006 | McGuckin, Jr. | A61B 17/0057 |
| | | | 606/213 |
| 2007/0191884 A1* | 8/2007 | Eskridge | A61B 17/12113 |
| | | | 606/213 |
| 2007/0198057 A1* | 8/2007 | Gelbart | A61B 17/0057 |
| | | | 606/213 |
| 2007/0249985 A1* | 10/2007 | Brenneman | A61B 17/083 |
| | | | 604/890.1 |
| 2007/0282352 A1* | 12/2007 | Carley | A61B 17/068 |
| | | | 606/142 |
| 2008/0312686 A1* | 12/2008 | Ellingwood | A61B 17/10 |
| | | | 227/179.1 |
| 2009/0082804 A1* | 3/2009 | Kato | A61B 17/1227 |
| | | | 606/213 |
| 2010/0228269 A1* | 9/2010 | Garrison | A61B 17/0057 |
| | | | 606/139 |
| 2010/0331866 A1* | 12/2010 | Surti | A61B 17/1114 |
| | | | 606/153 |
| 2011/0301618 A1* | 12/2011 | Lichtenstein | A61B 17/0057 |
| | | | 606/157 |
| 2012/0172927 A1* | 7/2012 | Campbell | A61B 17/12172 |
| | | | 606/213 |
| 2012/0209318 A1* | 8/2012 | Qadeer | A61B 17/0644 |
| | | | 606/213 |
| 2012/0283585 A1* | 11/2012 | Werneth | A61P 9/06 |
| | | | 606/200 |
| 2013/0046339 A1* | 2/2013 | Greenberg | A61B 17/0057 |
| | | | 606/213 |
| 2015/0039084 A1* | 2/2015 | Levi | A61F 2/2409 |
| | | | 623/2.38 |
| 2015/0080945 A1* | 3/2015 | Michalak | A61B 17/12172 |
| | | | 606/213 |
| 2017/0325824 A1* | 11/2017 | Li | A61B 17/12122 |
| 2018/0280006 A1* | 10/2018 | Rogers | A61B 17/0057 |
| 2019/0167242 A1* | 6/2019 | Rowe | A61B 17/064 |
| 2021/0059650 A1 | 3/2021 | Eidenschink et al. | |

* cited by examiner

OCCLUDER MEDICAL DEVICE

CROSS-REFERENCE TO RELATED APPLICATIONS

This application claims the benefit of priority to U.S. Provisional Patent Application No. 63/148,745, filed Feb. 12, 2021, the entire contents and disclosure of which are hereby incorporated by reference herein.

BACKGROUND OF THE DISCLOSURE

A. Field of Disclosure

The present disclosure relates generally to medical devices that are used in the human body. In particular, the present disclosure is directed to embodiments of an occlusion device that enables subsequent crossing of the septal wall after the occlusion device is deployed thereat. More specifically, the present disclosure is directed to an occlusion device with a device frame including a wire support structure with an incorporated cover coupled to the wire support structure.

B. Background

An occluder is a medical device used to treat (e.g., occlude) tissue at a target site within the human body, such as an abnormality, a vessel, an organ, an opening, a chamber, a channel, a hole, a cavity, a lumen, or the like. For example, an occluder may be used in trans-catheter secundum atrial septal defect closures. Secundum atrial septal defects are common congenital heart defects that allow blood to flow between the left and right atria of the heart, decreasing cardiac output. Occluders may be employed to block this blood flow.

Percutaneous procedures are becoming more prevalent in surgical practice. At least some percutaneous procedures access the left atrium through the septal wall. Conventional devices for closing Atrial Septal Defects (ASD) includes, for example, a braided-web closure device that is implanted in the septal wall, with braided-web disks on each side of the ASD that anchor the closure device. To cross the septal wall in a patient with previously closed ASD (e.g., to treat atrial fibrillation or place a Left Atrial Appendage closure device), a physician may need to navigate through the braided-web disks of the closure device, or remove the implanted device altogether.

Accordingly, it would be desirable to lessen or remove the presence of the braided-web disks, while maintaining the fundamental function and effectiveness of an occluder for closing an ASD.

SUMMARY OF THE DISCLOSURE

The present disclosure generally relates to medical devices and methods of manufacturing and use thereof, which facilitate the reduction in the amount of metallic material present in the device while maintaining the fundamental function and effectiveness of the medical device (e.g., an occlusion device).

In one embodiment, the present disclosure is directed to a medical device for treating a target site. The medical device includes a device frame including a proximal portion and a distal portion and configured to selectively transition between a collapsed configuration and an expanded configuration. The medical device also includes at least one cover, wherein at least one cover is coupled to at least one of the proximal and distal portions.

In another embodiment, the present disclosure is directed to a delivery system for deploying a medical device to a target site. The delivery system includes a medical device and a delivery device. The medical device includes a device frame including a proximal portion and a distal portion and configured to selectively transition between a collapsed configuration and an expanded configuration. The medical device also includes at least one cover, wherein at least one cover is coupled to at least one of the proximal and distal portions. The delivery device includes a delivery catheter, and a delivery cable within the delivery catheter and translatable with respect to the delivery catheter to advance the medical device through the delivery catheter to the target site.

In a further embodiment, the present disclosure is directed to a method for treating a target site including an atrial septal defect (ASD). The method includes providing a medical device having a preset, expanded configuration and a collapsed configuration, the medical device including a frame having a proximal portion and a distal portion and at least one cover, wherein at least one cover is coupled to at least one of the proximal and distal portions. The method also includes advancing the medical device to the ASD using a delivery system including a catheter and a delivery cable, positioning the medical device relative to the ASD to occlude blood flow; and de-coupling the medical device from the delivery cable to deploy the medical device.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
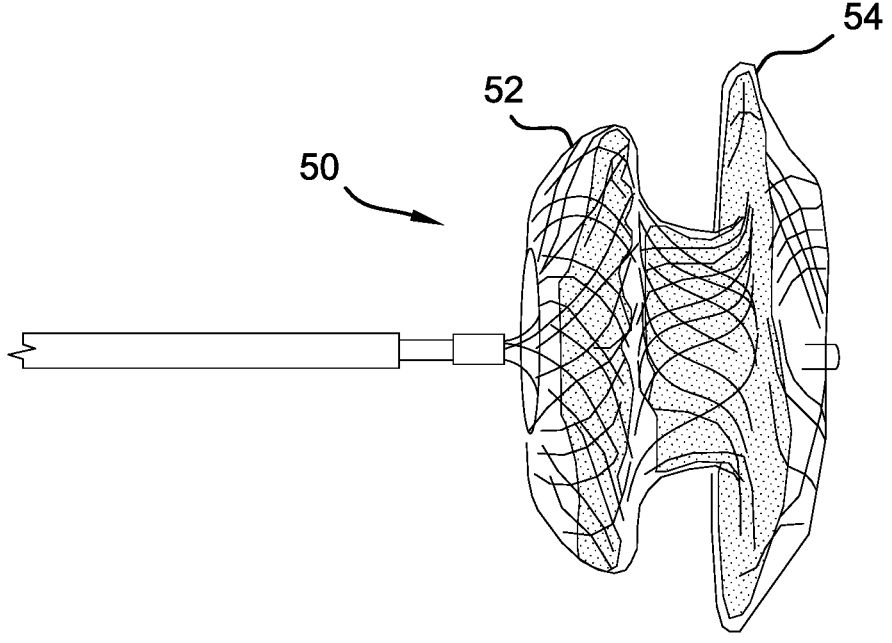
FIG. 1 illustrates a known medical device.

The present disclosure relates generally to medical devices that are used in the human body. Specifically, the present disclosure provides medical devices including occlusion devices having a device frame including a wire support structure having proximal and distal portions and at least one cover. The wire support structure may outline the septal defect while the cover may promote tissue ingrowth such that, after a period of time, the cover and tissue provide sufficient occlusion of the target site, without the need for braided-mesh disks. The occlusion devices of the present disclosure may minimize the amount of metallic material present in the device, compared to other known medical devices, which enables easier crossing of the atrial septal wall for future medical procedures once the device has been placed within the patient's body.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

It is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as an atrial septal defect, an LAA, a lesion, a vessel dissection, or a tumor. Embodiments of the medical device may be useful, for example, for occluding an LAA, ASD, VSD, or PDA, as noted above. Furthermore, the term "lumen" is also not meant to be limiting, as the vascular abnormality may reside in a variety of locations within the vasculature, such as a vessel, an artery, a vein, a passageway, an organ, a cavity, or the like. For ease of explanation, the examples used herein refer to the occlusion of a septal defect (e.g., an atrial septal defect or ASD).

As used herein, the term "proximal" refers to a part of the medical device or the delivery device that is closest to the operator, and the term "distal" refers to a part of the medical device or the delivery device that is farther from the operator at any given time as the medical device is being delivered through the delivery device. In addition, the terms "deployed" and "implanted" may be used interchangeably herein.

Some embodiments of the present disclosure provide an improved percutaneous catheter directed intravascular occlusion device for use in the vasculature in patients' bodies, such as blood vessels, channels, lumens, a hole through tissue, cavities, and the like, such as an atrial septal defect. Other physiologic conditions in the body occur where it is also desirous to occlude a vessel or other passageway to prevent blood flow into or therethrough. These device embodiments may be used anywhere in the vasculature where the anatomical conditions are appropriate for the design.

The medical device may include a wire support structure having proximal and distal portions that includes or is at least partially covered by a cover that acts as an occlusive material, while promoting native tissue growth, which is configured to substantially preclude or occlude the flow of blood. As used herein, "substantially preclude or occlude flow" shall mean, functionally, that blood flow may occur for a short time, but that the body's tissue growth to the cover results in occlusion or flow stoppage after this initial time period.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

In at least some conventional or known medical devices used for the occlusion of abnormalities, such as a medical device 50 shown in FIG. 1, include a proximal disk 52 and a distal disk 54, with a braided mesh configuration to facilitate thrombosis to seal a vascular abnormality. The mesh of the disks allows for the device to provide an occlusive effect. However, if the patient later requires a medical procedure that involves crossing over or through the implanted device, the physician must navigate through the braided material. This may increase the duration of a procedure and/or may adversely impact the sealing function of medical device 50, which may require an additional or extended procedure to implant a new medical device.

The medical devices of the present disclosure enable the closure and sealing of an abnormality while reducing the amount and optimizing the placement of metallic material implanted, compared to known devices. Accordingly, the medical device of the present disclosure reduces or eliminates the above-described disadvantages of known medical devices while providing a sufficient closure and sealing effect.

Figure 2:
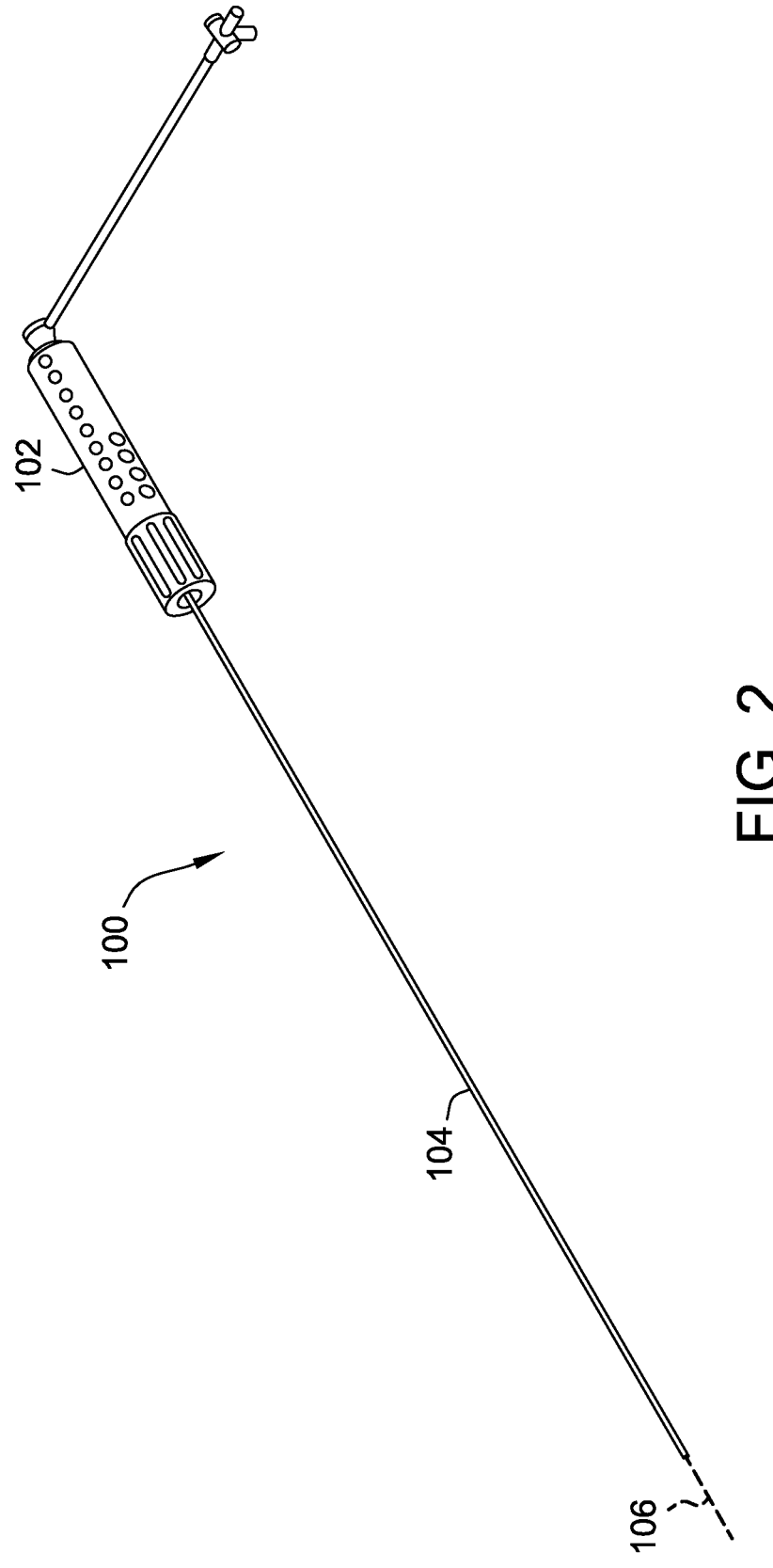
FIG. 2 is an exemplary embodiment of a delivery system for deploying a medical device in accordance with the present disclosure.

Turning now to FIG. 2, a schematic diagram of a delivery system 100 is shown. Delivery system 100 includes a delivery device 102 that includes a catheter 104 and a delivery cable 106 for deployment of a medical device at a target site. The medical device is deployed to treat the target site, and, in the example embodiment, is an occlusion device ("occluder").

Figures 3, 4:
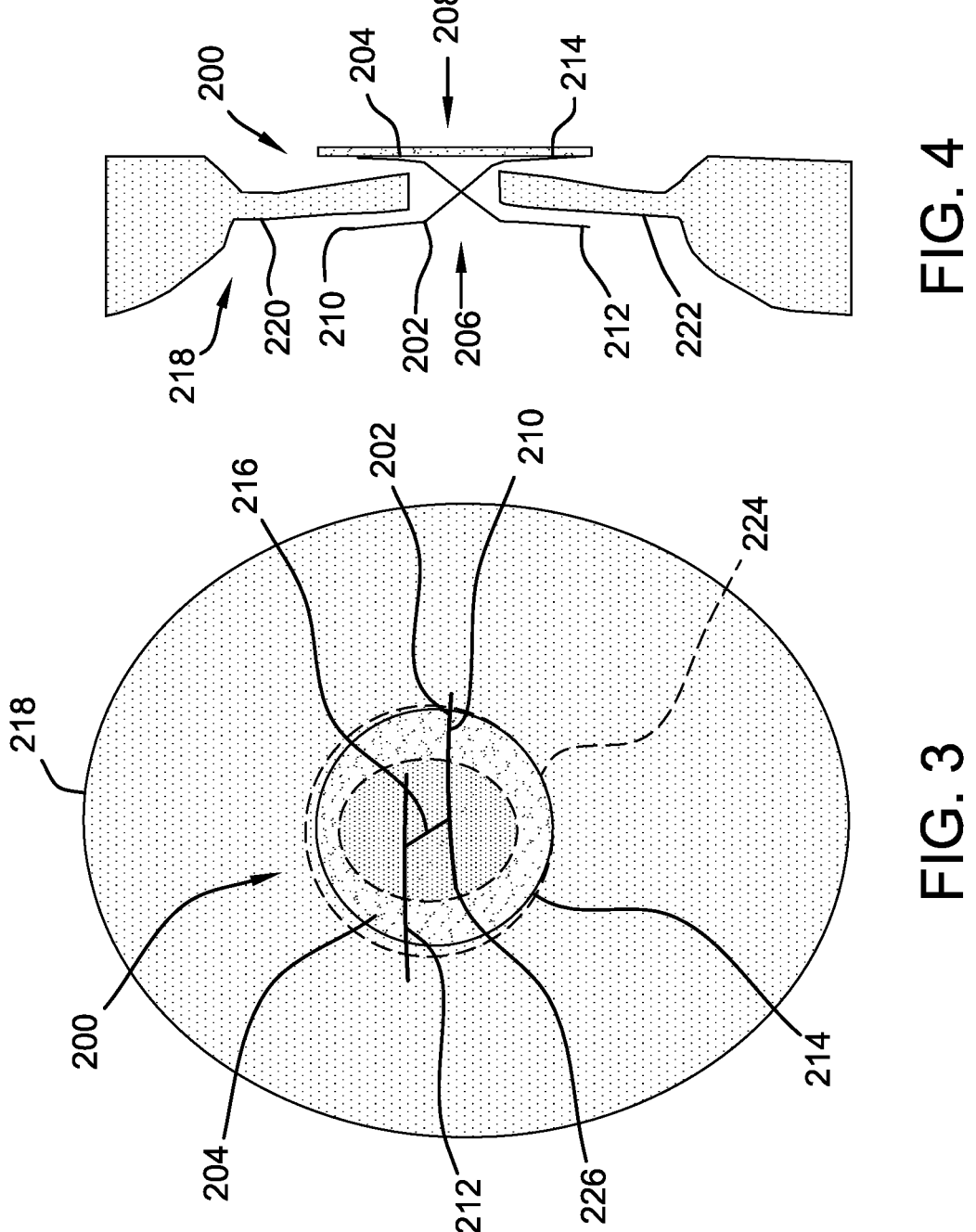
FIG. 3 illustrates a front sectional view of a first exemplary embodiment of a medical device including a frame having a wire support structure including at least one disk and a cover deployed at a target site, in accordance with the present disclosure.
FIG. 4 illustrates a side sectional view of the medical device shown in FIG. 3.

FIGS. 3 and 4 illustrate a first exemplary embodiment of a medical device 200. Specifically, FIG. 3 is a front sectional view of medical device 200, and FIG. 4 is a side sectional view of medical device 200. As shown in FIGS. 3 and 4, medical device 200 includes a device frame 202 and at least one cover 204. Device frame 202 includes a proximal portion 206 and a distal portion 208. In this exemplary embodiment, frame proximal portion 206 includes at least two wire legs 210, 212, and frame distal portion 208 includes a distal disk 214. Distal disk 214 may be collapsible in at least some example embodiments.

Wire legs 210, 212 extend proximally from distal disk 214. In particular, in the exemplary embodiment, wire legs 210, 212 are rotatably and/or hingedly coupled to distal disk 214 at distal ends thereof. In some embodiments, wire legs 210, 212 are connected at an intermediate portion thereof by a connecting segment 216. Connecting segment 216 is generally orthogonal to wire legs 210, 212, and extends therebetween to restrain movement of wire legs 210, 212 (e.g., preventing wire legs 210, 212 from extending undesirably away from one another). Wire legs 210, 212 may be formed by individual wires coupled to distal disk 214, for example, across a hinge component (not specifically shown). Alternatively, it is contemplated that device frame 202 may be a unitary component, and wire legs 210, 212 may extend from distal disk 214 at living hinges defined between distal disk 214 and wire legs 210, 212. In at least some embodiments, wire legs 210, 212 are coupled to distal disk 214 in an elastic manner, such that wire legs 210, 212 tend towards their expanded configuration (shown in FIGS. 3 and 4). The size and placement of wire legs 210, 212 may vary and is limited only by the ability to hold distal disk 214 against the septal tissue of the left atrium, as described further herein. In some embodiments, wire legs 210, 212 include tip features, such as barbs, hooks, and/or a texturized surface, at the tips thereof (e.g., at the proximal end thereof, opposite distal disk 214). These tip features may enhance engagement of wire legs 210, 212 with adjacent tissue and/or facilitate a more robust interface with the tissue, once medical device 200 is deployed at a target site.

Distal disk 214 has a peripheral edge 224; a diameter (not shown) of distal disk 214 is defined at peripheral edge 224. The diameter of distal disk 214 is selected to be greater than a diameter (not shown) of the ASD (or any other defect), defined at an outer edge 226 of the target site. It is contemplated that distal disk 214 may vary in size and shape, limited only by the ability of peripheral edge 224 of distal disk 214 to extend beyond outer edge 226 of the target site, ensure engagement with the tissue at the target site, as described further herein. Cover 204 extends across and is coupled to distal disk 214. As described further herein, cover 204 is formed from an occlusive material. Accordingly, when medical device 200 is deployed, cover 204 is configured to occlude blood flow therethrough.

In operation, wire legs 210, 212 are configured to extend from distal disk 214, through the target site (e.g., the ASD), and pivot into position to engage with septal tissue 218 of the right atrium. Specifically, medical device 200 is advanced to the target site within delivery catheter 104, and is advanced through a distal end of delivery catheter 104 using delivery cable 106 coupled to medical device 200. Medical device 200 is resheathable within delivery catheter 104 (e.g., to withdraw medical device 200 from the target site and/or adjust a position or orientation of medical device 200) at least until wire legs 210, 212 are deployed from delivery catheter 104. Once medical device 200 is deployed at a target site, wire legs 210, 212 deploy from their restricted configuration within delivery catheter 104 to their expanded, crossed configuration and into engagement with the surrounding septal tissue 218. In particular, one of wire leg 210 and wire leg 212 engages with relatively upper septal tissue 220 while the other of wire leg 210 and wire leg 212 engages with opposing, relatively lower septal tissue 222. It should be readily understood that "upper" and "lower" are used for clarity, with respect to the view of FIG. 4; wire legs 210, 212 may engage any opposing (e.g., approximately 180° separated) sections of septal tissue 218 depending on the final orientation of medical device 200 during deployment. Likewise, in embodiments of medical device 200 with more than two wire legs, the wire legs may engage sections of the septal tissue at any position.

Thereby, wire legs 210, 212 cooperate to retain distal disk 214 in tight engagement against septal tissue 218 within the left atrium. When distal disk 214 is tightly engaged with septal tissue 218, occlusive cover 204, coupled to distal disk 214, substantially occludes blood flow through the target side (e.g., the ASD).

Figure 5B:
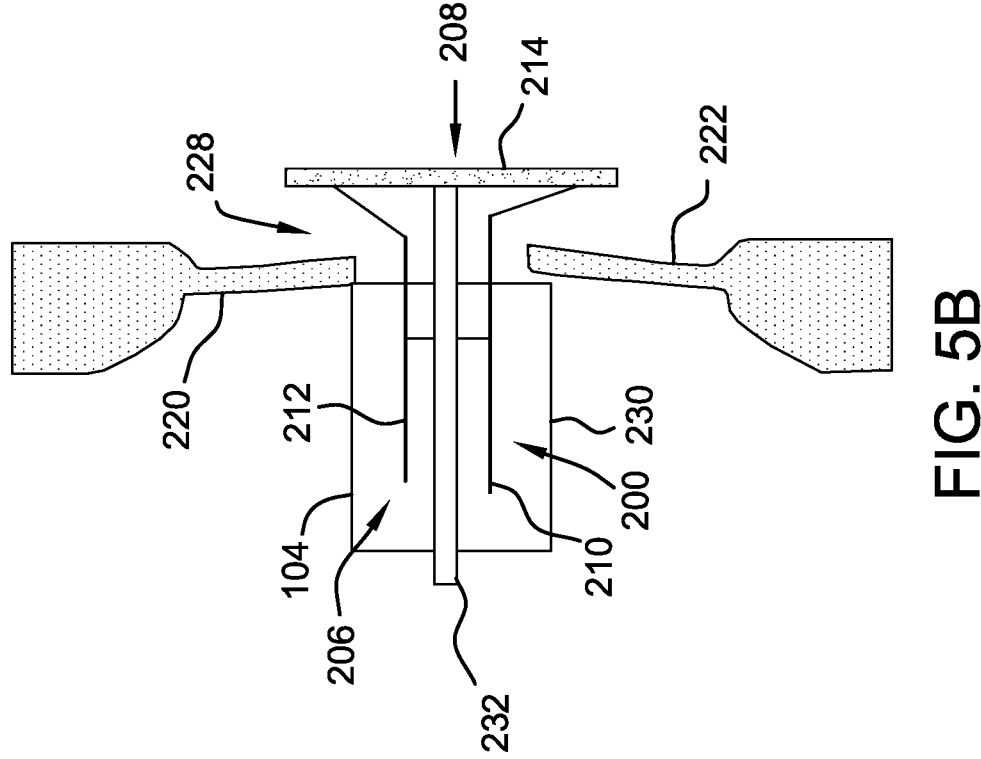
FIGS. 5A-5D illustrate one exemplary embodiment of deployment of the medical device as shown in FIG. 3 at a target site.
Figure 5A:
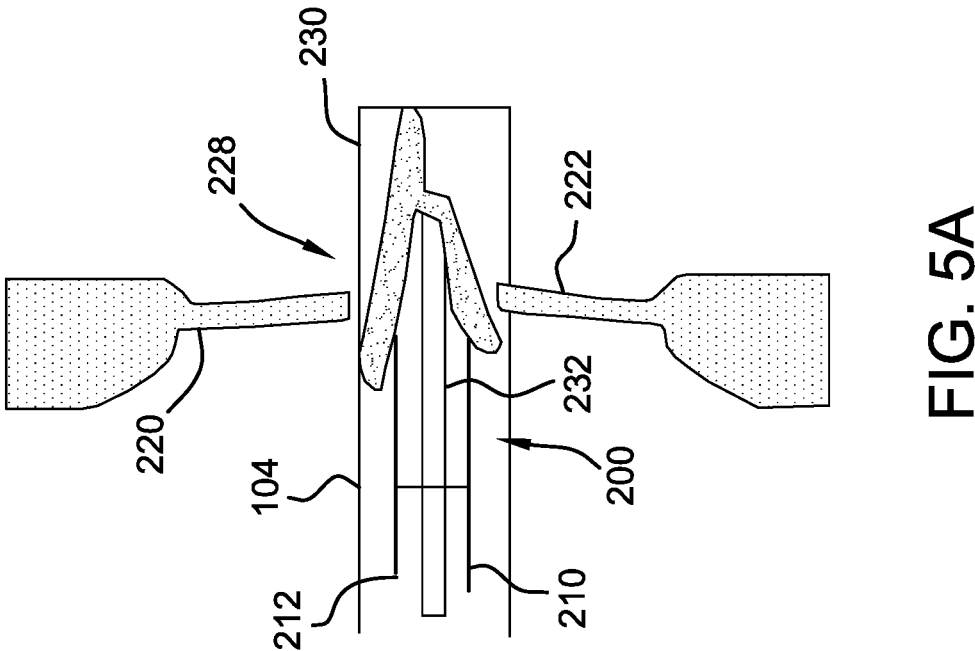

Turning now to FIGS. 5A-5D, an illustration of medical device 200, as shown in FIGS. 3 and 4, transitioning from a collapsed configuration to an expanded configuration during deployment of medical device 200 at a target site is provided. Delivery catheter 104 containing medical device 200 in a collapsed configuration is advanced towards a target site 228 (e.g., an ASD; see FIG. 5A). A distal end 230 of delivery catheter 104 is advanced through target site 228 (FIG. 5A), and, thereafter, delivery catheter 104 is retracted such that distal portion 208 of medical device 200 is deployed therefrom (FIG. 5B). In the illustrated embodiment, a push wire or rod 232 (which may be part of delivery cable 106, shown in FIG. 2, or separate therefrom) is engaged against a proximal surface of distal disk 214. Accordingly, as delivery catheter 104 is withdrawn, distal portion 208 is maintained in its deployed position at the distal or left side of the atrial septal wall. In some embodiments, push rod 232 may be coupled to wire legs 210, 212 as well, and may at least partially restrain legs 210, 212 within delivery catheter 104.

Figure 5D:
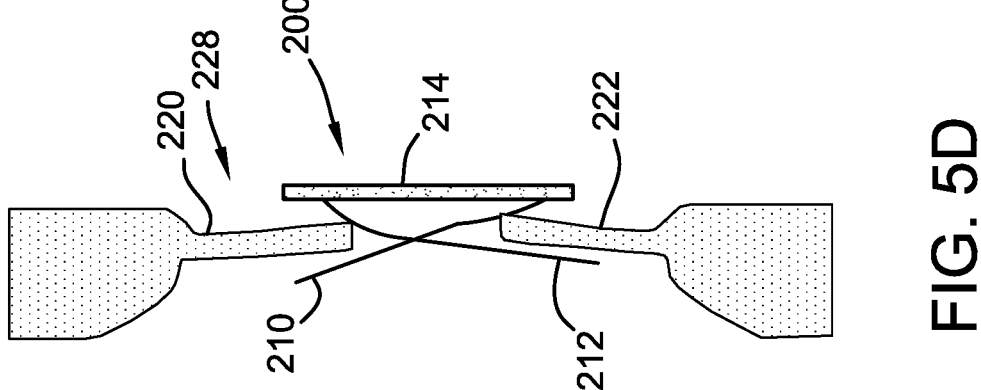
Figure 5C:
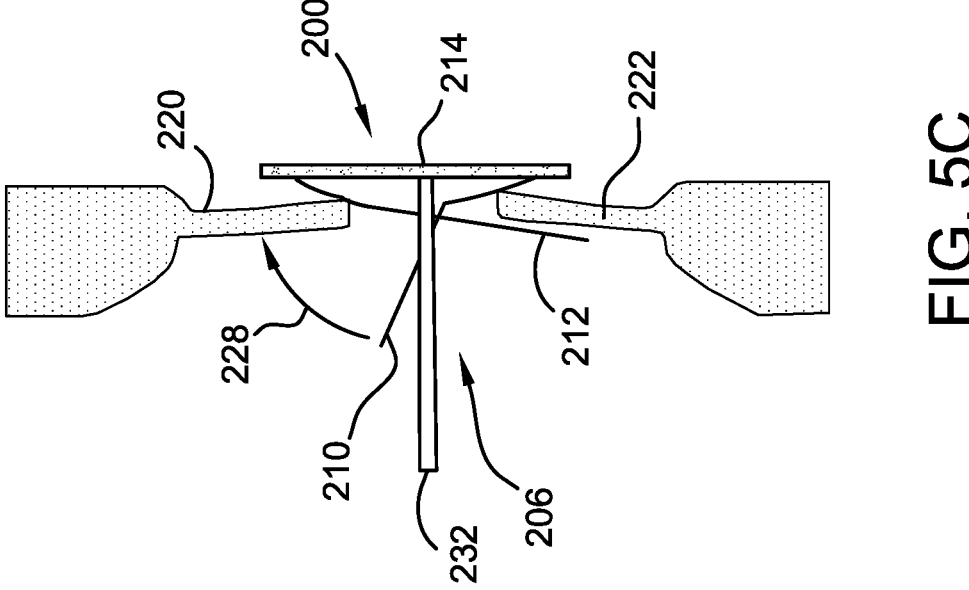

Distal portion 208 expands into its expanded configuration, in which distal disk 214 engages with tissue of the left atrial septal wall (FIG. 5B). Delivery catheter 104 is retracted further, until proximal portion 206 of medical device 200 is deployed therefrom (FIG. 5C). Once released from delivery catheter, wire legs 210 and 212 pivot into their expanded configuration and into engagement with upper and lower septal tissue 220, 222, respectively (FIG. 5D). Wire legs 210, 212 secure the placement of distal disk 214 within target site 228, thereby securing medical device 200 within target site 228. In some embodiments, as shown in FIG. 5C, push rod 232 remains engaged with medical device 200 (e.g., with a proximal side of distal disk 214) until wire legs 210, 212 are secured in place, to facilitate maintaining distal disk 214 in its deployed position. In other embodiments, where distal disk 214 has enhanced stability, push rod 232 may be withdrawn or retracted sooner, such as after distal disk 214 is deployed but prior to deployment of wire legs 210, 212.

Figure 7:
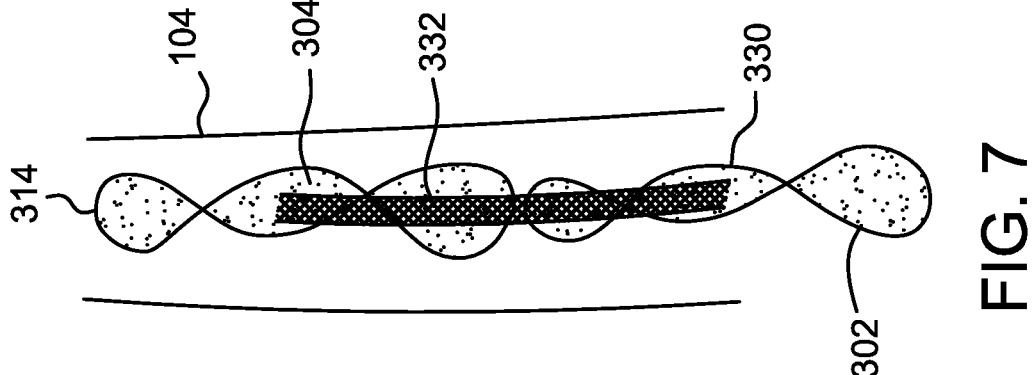
FIG. 7 illustrates a side sectional view of the medical device shown in FIG. 6 in a constricted configuration within a delivery catheter.
Figure 6:
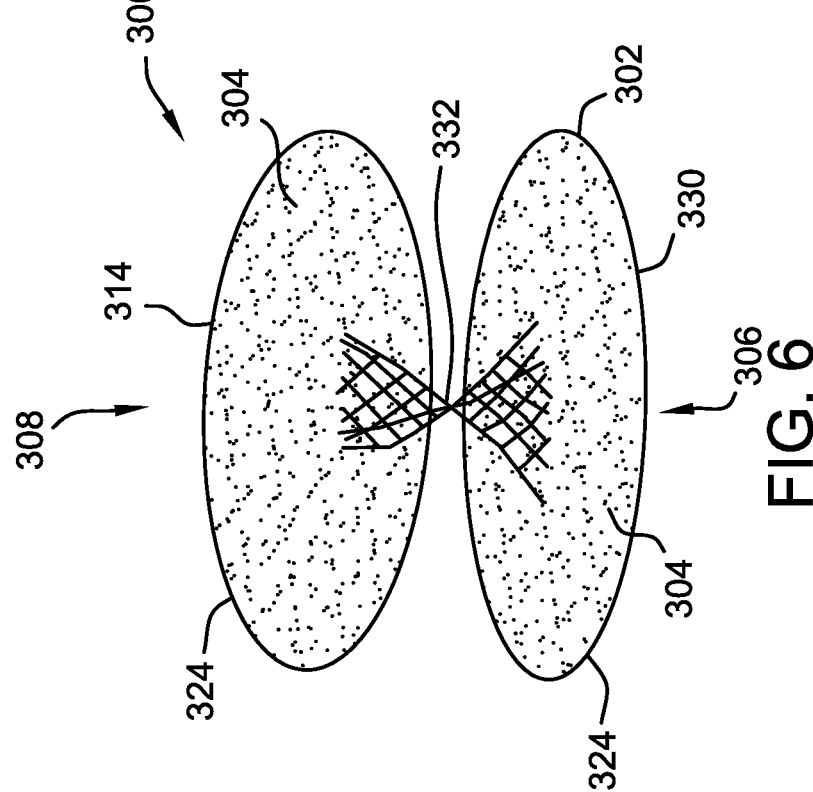
FIG. 6 illustrates a side sectional view of a second embodiment of the medical device in accordance with the present disclosure in an expanded configuration.

FIGS. 6 and 7 illustrate a second exemplary embodiment of a medical device 300. Specifically, FIG. 6 is a side sectional view of medical device 300 in an expanded configuration, and FIG. 7 is a side sectional view of medical device 300 in a constricted configuration within delivery catheter 104. Medical device 300, like medical device 200, includes a frame 302 and a cover 304, and frame 302 has a proximal portion 306 and a distal portion 308.

As shown in FIGS. 6 and 7, proximal portion 306 includes a proximal disk 330 and distal portion 308 includes a distal disk 314. Distal disk 314 is substantially similar to distal disk 214, shown in FIGS. 3-5D. In the embodiment of FIGS. 6 and 7, proximal disk 330 is substantially the same as distal disk 314—that is, any description of distal disk 314 also applies to proximal disk 330, and vice versa. Accordingly, in this embodiment, both distal disk 314 and proximal disk 330 have a respective cover 304 coupled thereto. Notably, in some embodiments, one of the distal disk 314 and the proximal disk 330 may have a different size than the other disk (e.g., one disk may be a few millimeters larger or smaller than the other), although the construction of disks 314, 330 remains otherwise the same. In the exemplary embodiment, each disk 314, 330 is larger than the defect to be occluded at the target site.

Proximal and distal disks 330, 314 are joined together by a waist member 332. In the exemplary embodiment, waist member 332 is coaxial with proximal and distal disks 330, 314. In other embodiments, waist member 332 is other than coaxial with (e.g., off-center with respect to) proximal disk 330 and/or distal disk 314. Waist member 332 is coupled to proximal and distal disks 330, 314 at cover 304. In the exemplary embodiment, waist member 332 is woven into cover 304. In other embodiments, waist member 332 is sutured to cover 304. It is contemplated that additional methods of incorporation would be suitable without departing from the scope of the disclosure. Waist member 332 may be formed by a stretchable fabric or other elastic and/or flexible material. The stretching characteristic of waist member 332 provides for resheathability and secure placement of medical device 300, as described further herein. In particular, waist member 332 is configured to apply continuous pressure on proximal and distal disks 330, 314, urging proximal and distal disks 330, 314 together when medical device 300 is deployed. It is further contemplated that waist member 332 may be formed from various materials and in various configurations, limited only by the ability of waist member 332 to connect proximal disk 330 to distal disk 314 and provide the necessary stretching and retention characteristics.

In this exemplary embodiment, frame 302 is formed from a pseudoelastic material that tends towards its expanded configuration (as shown in FIG. 6). In some embodiments, during delivery of medical device 300 to target site, medical device 300 is collapsed (e.g., for retention and delivery within delivery catheter 104, see FIG. 7) by twisting proximal disk 330 and distal disk 314. For example, each of proximal disk 330 and/or distal disk 314 may be twisted 180 degrees (e.g., to form two "lobes" that meet at a juncture formed by overlapping portions of twisted frame material forming the respective disk), 360 degrees (e.g., to form three lobes, each lobe meeting an adjacent lobe at a respective junction formed by overlapping portions of twisted frame material), and/or any other amount. In some embodiments, proximal disk 330 may also be rotated relative to distal disk 314 such that waist member 332 is also "twisted". Upon deployment at a target site, distal disk 314 is advanced from delivery catheter 104 and expands (e.g., "untwists") into its planar, expanded configuration. Once expanded, distal disk 314 engages with the septal tissue of the left atrium. Likewise, once proximal disk 330 is advanced from delivery catheter 104, within the right atrium, proximal disk 330 expands (e.g., untwists) into its planar, expanded configuration, and engages with the septal tissue of the right atrium. Waist member 332 urges proximal disk 330 and distal disk 314 towards one another and, thereby, retains proximal and distal disks 330, 314 in engagement with the septal tissue. Cover 304 substantially occludes blood flow therethrough.

Figure 8:
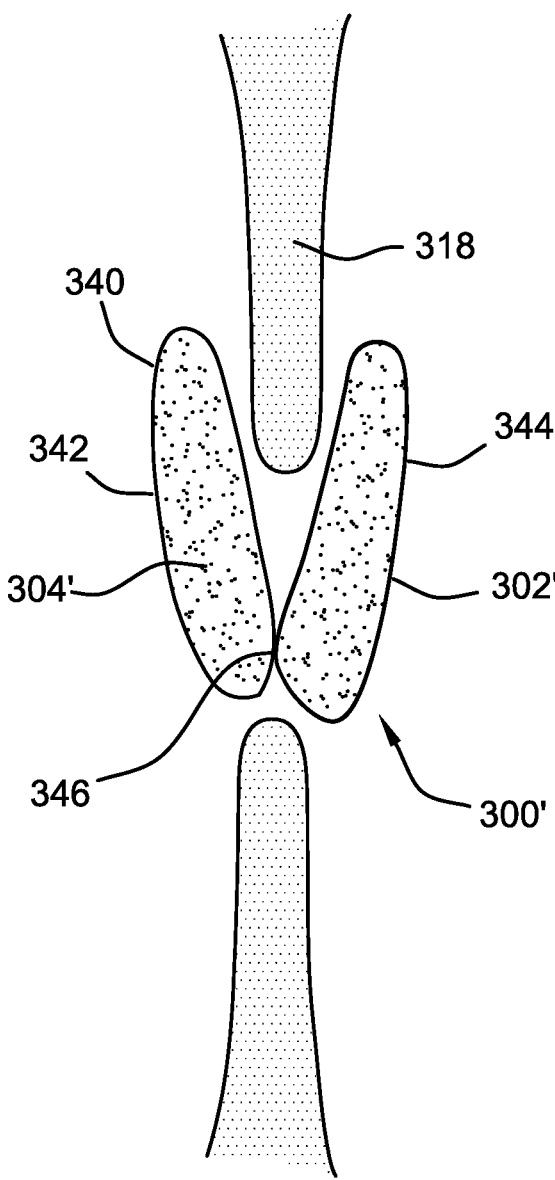
FIG. 8 illustrates a side sectional view of an alternative embodiment of the medical device shown in FIG. 6 deployed at a target site.

FIG. 8 depicts a variation of medical device 300, shown in FIGS. 6 and 7, and is therefore referred to with reference numeral 300'. In this embodiment, medical device 300' includes a frame 302' and a cover 304'. However, rather than having two discrete disks 330, 314, frame 302' defines a single, unitary disk 340. Disk 340 is similar to proximal disks 330, 314 and includes cover 304' coupled thereto. In contrast to the embodiment shown in FIGS. 6 and 7, however, disk 340 is configured to retain collapsed configuration during deployment of medical device 300'. In particular, disk 340 is configured to retain a twisted configuration, in which two opposing lobes 342, 344 are defined, specifically a proximal lobe 342 and a distal lobe 344, connected at a juncture 346 defined by the overlapping material of the twisted disk 340. Once medical device 300' is deployed, lobes 342, 344 are urged into engagement with the upper (or lower) septal tissue 318. Juncture 346 engages with an end surface of the opposing lower (or upper) septal tissue 318. Cover 304 substantially occludes blood flow therethrough.

Figures 9, 10:
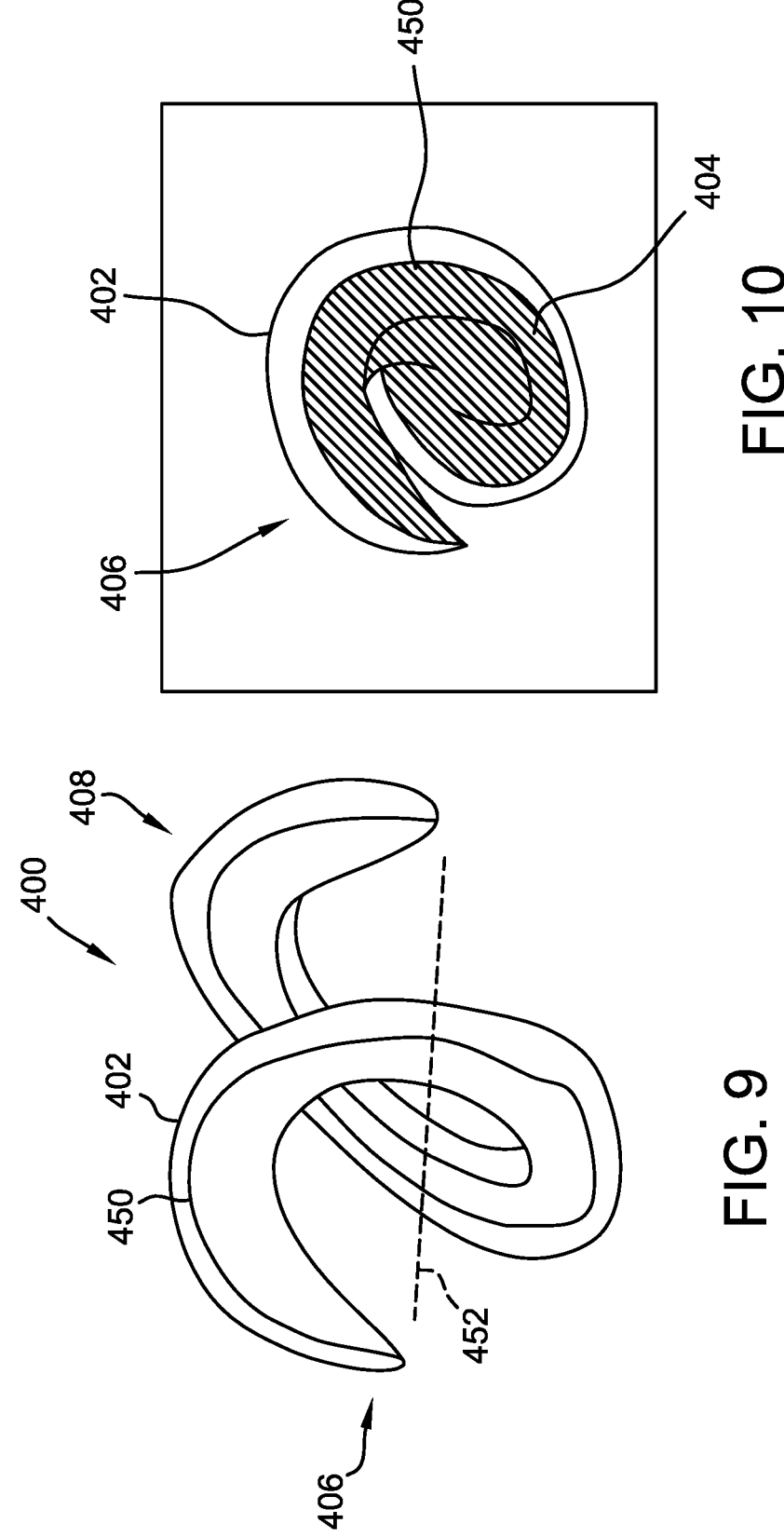
FIG. 9 illustrates a front perspective view of a third embodiment of the medical device in accordance with the present disclosure.
FIG. 10 illustrates a top plan view of the medical device shown in FIGS. 9.

FIGS. 9 and 10 illustrate a third exemplary embodiment of a medical device 400. Specifically, FIG. 9 is a front prospective view of medical device 400, and FIG. 10 is top plan view of medical device 400 deployed at a target site. Medical device 400 includes a frame 402 and a cover 404, and frame 402 has a proximal portion 406 and a distal portion 408. As shown in FIG. 9, device frame 402 is formed by a single wire. Frame 402 may be formed from an alternative material, such as a two-dimensional ribbon of material. Device frame 402 forms a spiral between and connecting proximal portion 406 and distal portion 408. The spiral may span at least 180°, such as, for example, 240°, 360°, or greater. Moreover, although one full coil (e.g., spanning approximately 360° is depicted in the embodiment of FIGS. 9 and 10, it should be readily understood that device frame 402 may include more than one full coil, and any amount of coil may be disposed on either side of the tissue at the target site. In some such embodiments, portions of the coil(s) may vary in diameter.

Cover 404 is coupled to frame 402 along one edge 450 thereof, such as an interior edge, relative to the spiral configuration of frame 402. Cover 404 may have a generally ribbon-shaped configuration, such that cover 404 extends from edge 450 of frame 402 towards an axis 452 of the spiral formed by frame 402.

Medical device 400 may be delivered to a target site in a collapsed configuration (not shown; e.g., using delivery catheter 104, shown in FIG. 2). Upon deployment, medical device 400 may expand to its expanded configuration (shown in FIG. 9). To deploy medical device 400, distal portion 408 is advanced through the target site (e.g., the ASD). As the delivery catheter is retracted, the spiral configuration of frame 402 keeps medical device 400 engaged with the tissue at the target site. Once deployed at an ASD, in the exemplary embodiment, distal portion 408 is configured to engage with the left atrial septal wall, and proximal portion 406 is configured to engage with the right atrial septal wall.

In any of the embodiments described herein, the device frame may be formed from a shape-memory material. One particular shape memory material that may be used is Nitinol. Nitinol alloys are highly elastic and are said to be "superelastic," or "pseudoelastic." This elasticity may allow the medical device to be resilient and return to a preset, expanded configuration for deployment following passage in a distorted form (e.g., through delivery catheter 104). Further examples of materials and manufacturing methods for medical devices with shape memory properties are provided in U.S. Publication No. 2007/0265656 titled "Multi-layer Braided Structures for Occluding Vascular Defects" and filed on Jun. 21, 2007, which is incorporated by reference herein in its entirety. It is also understood that the device frame may be formed from various materials other than Nitinol that have elastic properties, such as stainless steel, trade named alloys such as Elgiloy®, or Hastalloy, Phynox®, MP35N, CoCrMo alloys, metal, polymers, or a mixture of metal(s) and polymer(s). Suitable polymers may include PET (Dacron™), polyester, polypropylene, polyethylene, HDPE, Pebax, nylon, polyurethane, silicone, PTFE, polyolefins and ePTFE. Additionally, it is contemplated that the device frame may comprise any material that has the desired elastic properties to ensure that the device may be deployed and function as an occluder in a manner disclosed within this application.

In any of the embodiments described herein, the device cover 204 is coupled to, covers, and/or surrounds at least a portion of device frame. For example, in the embodiment shown in FIG. 4, cover 204 is coupled to peripheral edge 224 of distal disk 214. In the embodiment shown in FIG. 6, cover 304 is coupled to a peripheral edge 324 of proximal disk 330 and distal disk 314. In the embodiment shown in FIGS. 9 and 10, cover 404 is coupled to edge 450 of device frame 402. The cover may be coupled to the device frame by at least one suture, and/or by additional or alternative attachment means, without departing from the scope of the present disclosure.

The cover is formed from a bioresorbable or bioabsorbable fabric, knit or thin polymer material. The bioabsorbable polymer may include, for example, Poly-L-lactic acid (PLLA), Poly(glycolic acid) (PGA), Copolyesters of poly (e-caprolactone) (PCL), Trimethylene carbonate (TMC), Poly(d-diozanone) (PPDO), and combinations of various polymers. Additionally or alternatively, the biomaterial cover is formed from another polymer. The polymer may include, for example, PET (Dacron™), polyester, polypropylene, polyethylene, HDPE, Pebax, nylon, PTFE, polyolefins and ePTFE. In other embodiments, the cover may be formed from a tissue, such as pericardial tissues. The tissues may be derived from, for example, porcine, bovine, equine, and/or collagen matrices.

Further variations of the medical device described herein are contemplated. For example, it is contemplated that any medical device of the present disclosure device may incorporate a plurality of stabilization wires, which are configured to engage with the right atrial and/or and left atrial tissue when the medical device is deployed at the target site. Moreover, it is contemplated that although the figures provided herein depict medical devices with substantially round profiles, disks with alternative shapes and/or edge profiles may be implemented, such as disks with irregular or "wavy" profiles, which may enhance collapsibility of the medical device.

Figure 11:
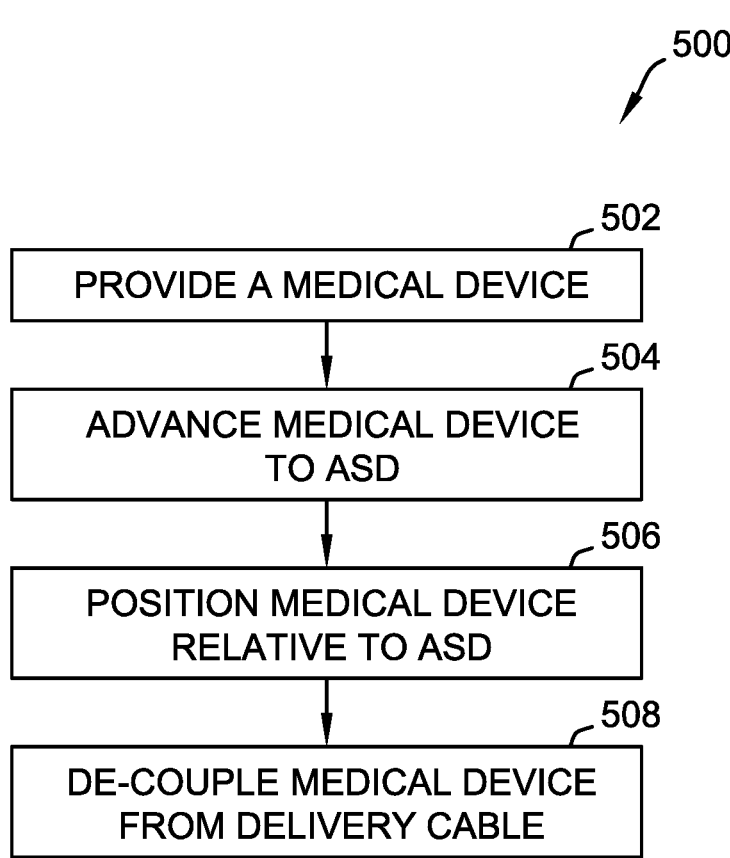
FIG. 11 is a flow diagram of an exemplary method of using a medical device to close an ASD.

Turning now to FIG. 11, a flow diagram of an exemplary method 500 of using a medical device (e.g., medical device 200, 300, 300', 400, all previously shown and described) to occlude an ASD in a patient is shown. In the exemplary embodiment, method 500 includes providing 502 a medical device. As described herein, the medical device includes a device frame comprising a proximal portion and a distal portion and configured to selectively transition between a collapsed configuration and an expanded configuration, and at least one cover, wherein at least one cover is coupled to at least one of the proximal and distal portions.

Method 500 also includes advancing 504 the medical device to the ASD using a delivery system including a catheter and a delivery cable, positioning 506 the medical device relative to the ASD to occlude blood flow, and de-coupling 508 the medical device from the delivery cable to deploy the medical device.

Method 500 may include additional, alternative, and/or fewer steps, including those described herein. For example, in some embodiments, positioning 506 the medical device relative to the ASD includes placing the distal portion of the medical device on the left atrial side of the ASD and the proximal portion on the right atrial side of the ASD.

Additionally, de-coupling 508 the medical device from the delivery cable includes the medical device transitioning from the constricted configuration adopted for delivery from a catheter to the preset expanded configuration.

While embodiments of the present disclosure have been described, it should be understood that various changes, adaptations, and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. A method for treating a target site including an atrial septal defect (ASD), the method comprising:
    providing a medical device having a preset, expanded configuration and a collapsed configuration, the medical device including a frame having a proximal portion and a distal portion and at least one cover, wherein the distal portion comprises a collapsible disk and the proximal portion comprises at least two wire legs, each wire leg respectively extending proximally between a distal end hingedly coupled at a hinge to a peripheral edge of the disk and a free proximal end, each wire leg folding along the hinge at the respective distal end thereof and into a crossed configuration when the device frame transitions from the collapsed configuration to the expanded configuration, and wherein at least one cover is coupled to the distal portion;
    advancing the medical device to the ASD using a delivery system including a delivery catheter and a delivery cable, while the medical device is in the collapsed configuration such that the collapsible disk is collapsed within the delivery catheter, a first wire leg of the at least two wire legs is within the delivery catheter and extends proximally from the collapsed disk and is positioned proximately to upper tissue of the ASD, and a second wire leg of the at least two wire legs is within the delivery catheter and extends proximally from the collapsed disk and is positioned proximately to lower tissue of the ASD;
    positioning the medical device relative to the ASD to occlude blood flow; and
    de-coupling the medical device from the delivery cable,

wherein positioning the medical device relative to the ASD to occlude blood flow includes first transitioning the medical device to a partially deployed configuration and then transitioning the medical device to the expanded configuration, wherein in the partially deployed configuration, the collapsible disk is expanded outside of the delivery catheter and is positioned on a right atrial side of the ASD, while the first wire leg remains within the delivery catheter and remains positioned proximately to the upper tissue and the second wire leg remains within the delivery catheter and remains positioned proximately to the lower tissue, and wherein, in the expanded configuration of the medical device, the collapsible disk is expanded outside of the delivery catheter, while the first wire leg is positioned outside of the delivery catheter and engages the lower tissue on a left atrial side of the ASD, and while the second wire leg is positioned outside of the delivery catheter and engages the upper tissue on the left atrial side of the ASD.

2. The method of claim 1, wherein the at least one cover is coupled to the device frame along the peripheral edge of the disk such that the at least one cover expands when the medical device transitions from the collapsed configuration into the expanded configuration.

3. The method of claim 1, wherein the at least two wire legs rotate towards the disk during the transition from the collapsed configuration to the expanded configuration.

4. The method of claim 1, wherein the device frame comprises a shape-memory material.

5. The method of claim 1, wherein the at least one cover is formed from one or more of: a fabric material, a knit material, a polymer material, a bioresorbable material, or a bioabsorbable material.

6. The method of claim 1, wherein the proximal portion further comprises a connecting segment extending between respective intermediate portions of the at least two wire legs, the connecting segment oriented parallel to the disk when the at least two wire legs are in the crossed configuration.

7. The method of claim 6, wherein, in the expanded configuration, respective proximal portions of the at least two wire legs, extending from the connecting segment to the respective free proximal end of the corresponding wire leg, are oriented parallel to the disk.

8. The method of claim 1, wherein, in the expanded configuration, the respective free proximal ends of the at least two wire legs are oriented radially outwards.

9. The method of claim 1, wherein the first wire leg and the second wire leg have free ends extending radially 180° opposite to one another in the expanded configuration.

10. The method of claim 1, wherein the delivery cable is engaged with a proximal surface of the at least one cover during delivery of the medical device.

11. The method of claim 1, wherein the delivery cable is configured to advance the distal portion of the device frame out of the delivery catheter prior to the proximal portion of the device frame during delivery of the medical device.

12. The method of claim 1, wherein said advancing comprises:

engaging the delivery cable against a proximal surface of the at least one cover; and advancing, using the delivery cable, the distal portion out of the catheter and into engagement with the left atrial side of the ASD.

13. The method of claim 12, wherein said advancing further comprises:

retracting the catheter to release the proximal portion of the medical device to engage the right atrial side of the ASD.

* * * * *